(12) United States Patent
Tayot et al.

(10) Patent No.: US 6,730,299 B1
(45) Date of Patent: May 4, 2004

(54) ADHESIVE PROTEIN FOAM FOR SURGICAL AND/OR THERAPEUTIC USES

(75) Inventors: Jean-Louis Tayot, La Tour de Salvagny (FR); Yves Bayon, Villeurbanne (FR); Philippe Gravagna, Irigny (FR); Michel Marie Dubois, Ste Foy les Lyon (FR)

(73) Assignee: Imedex Biomateriaux, Trevoux (FR)

( * ) Notice: Subject to any disclaimer, the term of this patent is extended or adjusted under 35 U.S.C. 154(b) by 122 days.

(21) Appl. No.: 09/787,543

(22) PCT Filed: Jul. 20, 2000

(86) PCT No.: PCT/FR00/02088
§ 371 (c)(1),
(2), (4) Date: Mar. 20, 2001

(87) PCT Pub. No.: WO01/05443
PCT Pub. Date: Jan. 25, 2001

(30) Foreign Application Priority Data

Jul. 21, 1999 (FR) .............................................. 99 09467
Jul. 21, 1999 (FR) .............................................. 99 09461

(51) Int. Cl.$^7$ ........................ A61K 38/51; A61K 39/395
(52) U.S. Cl. ........................ 424/101; 424/124; 424/177; 424/359
(58) Field of Search ................................. 424/101, 124, 424/177, 359

(56) References Cited

U.S. PATENT DOCUMENTS 4,442,655 A * 4/1984 Stroetmann
4,923,902 A * 5/1990 Wycech

* cited by examiner

*Primary Examiner*—Morton Foelak
(74) *Attorney, Agent, or Firm*—Stites & Harbison PLLC; B. Aaron Schulman

(57) ABSTRACT

A biocompatible fluid adhesive protein foam, which is bioresorbable and nontoxic, for surgical and/or therapeutic use, in particular for protecting/cicatrizing tissue wounds and for attaching biological tissues to each other or to an implanted biomaterial. The biocompatible fluid adhesive protein foam includes a biocompatible fluid adhesive protein matrix, which is bioresorbable and nontoxic, containing a biocompatible and nontoxic gas or mixture of gases. Further, a process and a kit for preparing such a foam are provided.

11 Claims, No Drawings

ADHESIVE PROTEIN FOAM FOR SURGICAL AND/OR THERAPEUTIC USES

The present invention lies within the domain of biological adhesives, which are biodegradable and nontoxic, intended for surgical and/or therapeutic use.

More specifically, the present invention relates to a biocompatible fluid adhesive protein foam, which is bioresorbable and nontoxic, for surgical and/or therapeutic use.

It also relates to such a foam containing bioactive substances which can be released in a given site.

The invention relates, moreover, to a process for producing such an adhesive foam and to a kit for the preparation thereof.

It also relates to the use of the adhesive foam in surgery and/or for therapeutic purposes, in particular for protecting wounds and attaching biological tissues to each other or to an implanted biomaterial.

Biological glues which can adhere to tissues or attach them to each other, in a few minutes, without using staples or sutures are known. These glues are eliminated, in general after the cicatrization of the wound, by biodegradation, resorption or by simple detachment in the form of scabs.

Various technologies have been developed for the formulation of tissue adhesives. Some of them are of synthetic origin, such as the glues based on cyanoacrylates (2-butyl cyanoacrylate, 2-octyl cyanoacrylate), or on synthetic polymers, and others contain biological materials such as collagen or fibrin.

In general, the synthetic adhesives are used for the tight sealing of vessels or of lungs and for "gluing" the edges of skin incisions. The adhesive biological derivatives such as collagen and fibrin in addition have hemostatic properties and also act by controlling bleeding.

The cyanoacrylate glues form toxic products when degrading, even though the glues recently developed are less harmful.

They lead to products which are brittle after polymerization on the site of application. They remain in place 7 to 10 days and are eliminated by simple detachment, after cicatrization. Their polymerization time is relatively unmodifiable, less than 1 minute, and does not allow flexible use of these glues. They can also easily run and, consequently, glue tissues adjacent to the desired site.

FOCAL (U.S. Pat. No. 5,844,016) has described synthetic adhesives based on the photochemical polymerization of hydrogel made of polyethylene glycol (PEG). Their method of use is not practical. Specifically, they involve application in several steps, to the operating site, of the solution containing the photochemical initiator (eosin Y) and of the monomer (derivative of PEG and of acrylate) solution possibly containing a biologically active substance, and then irradiation with light until a solid transparent and adherent gel is obtained, after 40 to 60 seconds. This type of adhesive thus requires the application of several solutions which, because of their fluidity, can easily spread over sites adjacent to the target site.

These adhesives have also been described for the targeted delivery of biologically active substances (vascular endothelial growth factor [VEGF], endothelial cell growth factor [ECGF], basic fibroblast growth factor [bFGF], bone morphogenic protein [BMP], etc) contained in their microparticulate network (FOCAL U.S. Pat. No. 5,879,713).

BARD (WO 97/42986) has described an adhesive similar to that of FOCAL, mentioned above, for which the polymerization is induced by ultraviolet rays.

COHESION TECHNOLOGIES (U.S. Pat. No. 5,874,500; U.S. Pat. No. 5,744,545; U.S. Pat. No. 5,550,187) has also described liquid glues based on activated PEG (ex. PEG comprising succinimidyl and maleimidyl groups) which polymerize after simple application to the target site of application, in a varying amount of time. These glues are potentially toxic and have the drawback of being fluids, which prevents accurate application to the site of intervention.

CRYOLIFE has developed another type of adhesive, based on a mixture of bovine albumin and of glutaraldehyde. Besides the known toxic effects of this crosslinking agent and of the antigenic nature of the bovine albumin, this adhesive also has the abovementioned problems of fluidity.

Fibrin glues, a mixture of concentrated fibrinogen and of thrombin, create a fibrin matrix which is slowly degraded by the endogenous fibrinolytic system. Before polymerization, they are very fluid and can easily run, even though their reaction time can be adjusted by modifying the total amount of thrombin. They can release active biological substances (ex. Zarge et al., J. Surg. Res., 1997, 67, 4–8; Greisler et al., Surgery, 1992, 112, 244–255; Gray et al., Surg. Forum, 1993, 44, 394–396; Clinica, 1999, 848, 18).

Devices combining fibrin glues with liposomes have also been described (U.S. Pat. No. 5,651,982).

Fibrin glues can be vaporized onto the site of application, using a spray, and can form a foamy coagulum film (U.S. Pat. No. 5,607,694; WO 97/33646).

Complex devices combining a synthetic polymer protein with a crosslinking agent have been provided as biological adhesives (U.S. Pat. No. 5,817,303).

Finally, several adhesives based on collagen or on gelatin have been described in the literature. Very early on, gelatin was combined with resorcinol and with formaldehyde or with glutaraldehyde to produce an adhesive also having hemostatic properties (Tatooles et al., Surgery, 1966, 60, 857–861; Braunwald et al., Surgery, 1966, 59, 1024–1030; Guilmet et al., J. Thorac. Cardiovasc. Surg., 1979, 77, 516–521). With this type of adhesive, there is, however, a risk of release of formaldehyde or of glutaraldehyde causing toxic reactions, leading to tissue necroses or less severe reactions, producing poor cicatrization or the slowing down thereof.

In certain formulations, the collagen is closely associated with thrombin (CoStasis from Cohesion technol. and Flo-Seal from Fusion).

For applications in surgery, it can also be modified chemically with acylation or sulfonation agents so that the collagen thus transformed can polymerize on the site of application, in the presence or absence of an initiator (U.S. Pat. No. 5,874,537; WO 97/42986).

An adhesive obtained using heated collagen and, as crosslinking agent, a biodegradable macromolecular polyaldehyde has also been described (FR 2,754,267; FR 2,754,268).

The glues for surgical and/or therapeutic use, described in the literature, are essentially in liquid form.

A noninjectable lyophilized material comprising the elements of the fibrin glue (thrombin and fibrinogen) has been described (U.S. Pat. No. 4,442,655). An inert gas is optionally introduced into the fibrinogen/thrombin reactive aqueous solution in order to lighten the material which has a hemostatic role or a role of support for the delivery of cicatrizing substances, and is mainly intended for the cleaning of wounds. Another noninjectable lyophilized material comprising, inter alia, the elements of the fibrin glue and collagen has also been described in the literature, as an effective hemostatic agent and an adhesive (Nishida et al., Geka Shinryo [Surgical Diagnosis Treatment], 1994, 36, 1449–1459; Ochiai et al., Sanpujinka no Jissai [Obstetric and Gynecologic Practice], 1995, 44, 253–262; Schelling et al., Ann. Surg., 1987, 205, 432–435; Shimamura et al., The Clinical Report, 1994, 28, 2994–2507).

Some adhesives have also been proposed in the form of a spray so as to allow a more homogeneous and more discreet application over a considerable surface area. However, the use of a spray has drawbacks, including:

i) the contribution of not insignificant amounts of carbon dioxide or of other gases, leading to risks of dangerous very high pressure and possibly proving to be toxic for applications in noninvasive surgery, ii) the considerable displacement of the adhesive mixture over the site of deposit by the propellent gas of the applicator, iii) the development of a special spray applicator, markedly increasing the cost price of the adhesive device and:possibly requiring a more complex environment, in particular because of the connection of the device to a source of propellent gas.

Moreover, rigid protein foams are known which are obtained by introducing a gas (air) into a solution of proteins, and then drying the foamy mass at high temperature, for panels of thermal insulating foam (U.S. Pat. No. 2,584,082).

A foam resulting, from the stirring of a solution of proteins in the presence of air or another inert gas has also been incorporated in cosmetic creams (CH 674 804).

Also known are polysaccharide foams which are obtained by mixing with shearing, after introduction of a gas into the solution of polysaccharides, and which can be applied by spraying for the cicatrization of wounds or as postoperative antiadhesion barriers (EP 747 420).

No property of adhesion to wounds or organs has been described for these foams.

An objective of the invention is to provide an adhesive which does not have the major drawbacks mentioned above, in particular risks of toxicity, difficulties of application in particular due to fluidity, to application in several steps and to the time of reactivity of the components, use of propellent gases (sprays), etc.

An objective of the invention is thus to provide an adhesive which is fluid and optionally injectable, biocompatible, bioresorbable and nontoxic, suitable for surgical and/or therapeutic use and stable over time, and which can be conserved under relatively simple conditions.

An objective of the invention is also to provide such an adhesive for attaching biological tissues, including live tissues, to each other or to an implanted biomaterial, or for filling tissue cavities or protecting tissue wounds.

An objective of the invention is also to provide such an adhesive in a ready-to-use form, which is simple and practical to use and, in particular, which can be injected with the aid of catheters or cannulas.

Another objective of the invention is to provide an adhesive the structure of which facilitates tissue colonization.

Another objective is to provide an adhesive the biodegradability of which is controllable over time, after application.

Another objective of the invention is to provide an adhesive possibly containing biologically active substances.

An objective of the present invention is, moreover, to provide a process for preparing such an adhesive, which is easy to carry out and without danger for the recipient organism.

An objective of the invention is also to provide kits which allow simple and rapid preparation of such an adhesive.

These objectives, and others which will emerge from the description given hereinafter, are attained with the aid of a biocompatible fluid adhesive protein foam, which is bioresorbable and nontoxic, for surgical and/or therapeutic use, in particular for attaching biological tissues to each other or to an implanted biomaterial and protecting/cicatrizing tissue wounds, characterized in that it comprises a biocompatible fluid protein adhesive matrix, which is bioresorbable and nontoxic, containing a biocompatible and nontoxic gas or mixture of gases.

A subject of the invention is also a process for preparing an adhesive foam as mentioned above, characterized in that it comprises extemporaneously mixing, in a homogeneous manner, a biocompatible and nontoxic gas or mixture of gases with a fluid material of a biocompatible adhesive protein matrix, which is bioresorbable and nontoxic, or with one of the basic constituents of such a material.

A subject of the invention is also a kit for preparing such an adhesive foam, characterized in that it comprises constituents for forming a biocompatible adhesive fluid protein matrix, which is resorbable and nontoxic, a biocompatible and nontoxic gas or mixture of gases, and means for extemporaneously mixing said constituents for forming the adhesive matrix and said gas or mixture of gases.

The inventors have demonstrated, surprisingly, that fluid and adhesive foams can be prepared by extemporaneously incorporating a gas or mixture of gases into biological "glues", so as to produce ready-to-use protein foams which can be applied in particular by injection, using various devices such as cannulas or catheters.

The inventors have demonstrated, entirely surprisingly, the possibility of producing a biocompatible adhesive protein foam which is bioresorbable and nontoxic, fluid and injectable, and suitable for surgical and/or therapeutic use, using a protein compound either in a form solubilized in aqueous medium or in a solid form, in particular a form lyophilized or dried with a volatile solvent.

The inventors have shown, entirely unexpectedly, that such foams have properties of adhesion, in particular to biological tissues, including live tissues, comparable to biological "glues" in liquid form, while at the same time being more elastic, and are perfectly tolerated by the recipient organism. They can conserve their adhesive properties until they have completely degraded.

They have also discovered that such foams have unexpected characteristics of rapid and effective colonization by cells of the recipient organism.

They have also discovered, just as unexpectedly, that such adhesive foams may be applied with great accuracy to biological tissues, for their attachment to each other or to an implanted biomaterial having functions reactive with respect to the adhesive matrix, without experiencing the problems of running conventionally encountered with liquid biological glues, or the risks of dispersion of the glues by the propellent gases of the sprays. The deposits of these adhesive foams on the tissues are also easier to visualize due to their particular microporous texture and to their opacity, these being characteristics which differ very markedly from the conventional liquid glues and from human or animal tissues.

They have also shown that certain formulations of these foams lose their "sticky" nature on their external surface, after polymerization of the adhesive agents, allowing selective and accurate application of these foams to the target tissues without gluing undesired tissues.

They have also discovered that it is possible to easily incorporate into these adhesive foams biologically active substances optionally combined with a vehicle which protects them, at least partially, against chemical modifications possibly caused by the polymerization agents.

The present invention will be described in more detail hereinafter.

According to the invention, the expression "adhesive protein matrix" is intended to mean a network formed from one or more protein components which have adhesive properties and which are nontoxic, biocompatible and biodegradable, said network containing a biocompatible and nontoxic gas or mixture of gases.

The adhesive properties of the matrix are generally acquired by a process of polymerization and/or of crosslinking of its basic constituent (s), preferably initiated by one or more polymerization/crosslinking agent(s) supplied before the formation of the foam.

The term "nontoxic" is intended to mean any product the toxicity of which is sufficiently low to allow use in surgery and/or in therapeutics for the human or animal body, whatever the site of application, while satisfying the criteria and standards imposed by the legislation.

The term "biodegradable" is intended to mean any component capable of disappearing by progressive degradation (metabolization).

The adhesive matrix can correspond, from the point of view of its chemical composition, to known biological adhesives and glues.

It can thus consist of or comprise a protein compound (basic constituent), at least partially polymerized/crosslinked, which is nontoxic, biocompatible and biodegradable, and which has adhesive properties.

The expression "protein compound" refers to a protein or mixture of proteins optionally chemically modified, in particular by methylation or succinylation.

The invention thus extends to adhesive matrices produced using a composition comprising, on the one hand, a protein compound (basic constituent) which can be polymerized/crosslinked and which is potentially adhesive and, on the other hand, a polymerization/crosslinking agent, by mixing them extemporaneously before use.

In accordance with the invention, the expression "protein compound which can be polymerized/crosslinked and which is potentially adhesive" is intended to mean any protein compound as defined above capable of developing, in the presence of water, adhesive properties by polymerization and/or crosslinking under the effect of a polymerization/crosslinking agent.

According to the invention, the polymerization/crosslinking agent can comprise a compound or mixture of compounds compatible with the protein compound which can be polymerized/crosslinked so as to cause the polymerization of the latter by extemporaneous mixing, generally in a few minutes.

The protein compound is used either in a form solubilized in aqueous medium or in the form of a solid, in particular of a powder or of fibers.

The polymerization/crosslinking agent can also be used in a form solubilized in aqueous medium or in a pulverulent form, preferably a lyophilized form.

The proteins used for the purposes of the invention are preferably selected from collagen, gelatin, albumin, elastin and fibrinogen, and more preferably from collagen and albumin. Collagen is most particularly preferred.

The collagen used for the purposes of the invention can be equally of human or animal origin, or obtained by means of genetic recombination. It can be type I, III, IV or V collagen, or a mixture thereof in any proportion.

It can be native collagen, i.e. collagen which has conserved its helical structure of origin, optionally chemically modified by methylation, by succinylation or any other known method, in particular to make it more soluble at physiological pH, or treated to eliminate telopeptides, in particular by pepsin digestion.

It is also possible to use nonhydrolyzed collagen consisting mainly of a chains the molecular weight of which is close to 100 kDa. In this case, the helical structure of the collagen is denatured, at least partially, for example by moderate heating, in the presence of water, in particular to a temperature of between 40 and 70° C., under gentle conditions so as to avoid the degradation by hydrolytic cleavage of the gelatin thus formed, generally less than 10% of the collagen chains having a molecular weight lower than 100 kDa.

Such a gelatin is called hereinafter "heated collagen", in order to distinguish it from commercially available gelatin which can also be used for the purposes of the invention, but in a nonpreferred way.

The native collagen or the heated collagen described above is used either in the form of fibers or dry powder, or in the form of an aqueous solution at a concentration of between 1 and 5%, preferably between 2.5 and 4%, by weight for the native collagen, and between 4 and 20%, preferably between 5 and 16%, by weight for the heated collagen.

The pH of the solutions of native collagen or of heated collagen is preferably neutral, more preferably between 6 and 8.

When the adhesive matrix is obtained using albumin, it is preferably used in the form of dry powder or in the form of an aqueous solution at a concentration of between 20 and 50% by weight, preferably 40 to 50%.

In the case of fibrinogen, a powder or an aqueous solution at a concentration of between 10 and 20% is preferably used.

In accordance with the present invention, the crosslinking agent can be selected from natural or synthetic reactive polymers, preferably with a molecular weight greater than 1 000, such as macro-molecular polyaldehydes or hydrophilic polymers, the subsequent diffusion of which from the glue is hindered by the considerable molecular weight, preventing an immediate direct toxicity.

The expression "reactive polymers" is intended to mean polymers capable of reacting with the protein compounds as defined above, in particular with respect to amine or sulfhydryl functions which they may contain.

The macromolecular polyaldehydes which can be used according to the invention comprise biodegradable polyaldehydes of natural origin, i.e. any compound having several aldehyde functions derived from a biodegradable natural polymer.

The polyaldehydes can be used alone or as a mixture, the term "polyaldehyde" used herein referring equally to a compound alone or a mixture of several of these compounds.

These macromolecular polyaldehydes can be prepared by oxidation of polysaccharides or of mucopolysaccharides, in particular with periodic acid or a salt thereof, according to a process known per se.

Among the polysaccharides or mucopolysaccharides suitable for the preparation of the invention, mention may be made of starch, dextran, agarose, cellulose, chitin, chitosan, alginic acid, glycosaminoglycans, hyaluronic acid and chondroitin sulfate, or the derivatives thereof. Starch, dextran or hyaluronic acid are preferred, starch being most particularly preferred.

The polyaldehyde can be obtained by adding a solution of periodic acic or a salt thereof to the solution of polysaccharide or mucopolysaccharide, until a final concentration of between 0.01 and 1 M, preferably between 0.25 and 0.5 M is obtained. The oxidation step can be carried out on solutions, gels or suspensions of polysaccharide(s).

The preparation of oxidized polysaccharide can then be subjected to dialyses, diafiltrations, filtrations and ultrafiltrations, for the purpose of eliminating the oxidation reaction products and reagents, as well as iodinated derivatives formed during the reaction, or in excess.

Before use, the oxidized polysaccharide or mucopolysaccharide is preferably conserved in an acid solution, at the pH that it acquires spontaneously, at a concentration of between 0.5 and 20% by weight, preferably between 1 and 10%.

The solution is stable in the absence of air and is conserved preferably between +1° C. and +25° C.

In one variant, the oxidized polysaccharide or mucopolysaccharide can be in an acid lyophilized form, the redissolving of the lyophilizate possibly being in water or with the required physiological buffer.

The hydrophilic polymers useful for the purposes of the invention preferably have a molecular weight of 1 000 to 15 000 Da, preferably between 2000 and 5 000. They comprise, for example, derivatives of poly(ethylene) glycol (PEG), poly(oxyethylenes), poly(methylene glycols), poly(trimethylene glycols) and poly(vinylpyrrolidones), derivatives of PEG being the most preferred. They can be linear or branched, but are not highly crosslinked. Poly(oxyethylene)-poly(oxypropylene) block polymers optionally having an ethylenediamine core (polymer with 4 chain ends) may also be suitable.

The hydrophilic polymers are "activated" so as to react selectively with the amines and thiols of the proteins. At the end of the chains of the polymers, there is a structure similar to; -polymer chain-binder-LG (leaving group) for the polymers reacting with the amines, or -polymer chains-GRT (group reactive with respect to thiols) for the polymers reacting with the thiols.

The binder can be selected from groups consisting of a carbonate —C(O)—, a monoester —R—CH$_2$—C(O)— or a diester —C(O)—O—(CH$_2$)$_n$—O—C(O)—; the LG can be a succinimidyl, maleimidyl, phthalimidyl, imidazolyl, nitrophenyl or tresyl derivative, the succinimidyl derivative being the most preferred. Finally, the GRTs can be selected from vinylsulfone, iodoacetamide, maleimide, and orthopyridyl disulfide derivatives.

These hydrophilic polymers are synthesized according to methods known to those skilled in the art.

They can be conserved in dehydrated form, packaged in syringes.

For the production of the adhesive matrix according to a first embodiment, the abovementioned protein compounds, in particular the collagen, the heated collagen or the albumin, can be in aqueous solution. They are mixed extemporaneously with the polymerization/crosslinking agent, under conditions such that the polymerization/crosslinking of said protein compounds can take place in a time of preferably less than 5 minutes.

According to a second embodiment for the production of the adhesive matrix, the abovementioned protein compounds, in particular the collagen, the heated collagen or the albumin, can be in the form of a solid, in particular of a dry powder, optionally sterilized, for example in a first syringe. In this embodiment, it is preferred to plan an additional step to solubilize the powder before introducing the polymerization/crosslinking agent. A second syringe containing a buffered aqueous solution can then be used. One at least of the two syringes is associated with heating means in order for the mixture to be reheated to a temperature of 37 to 50° C.

The protein compound is dissolved by successively transferring the contents of the two syringes from one to the other, making best use of the possibility of reheating which facilitates the rapid solubilization of the protein compound.

When the mixture is in homogeneous aqueous suspension, it is then possible to introduce the crosslinking agent so as to continue the preparation and the application of the adhesive protein foam as in the first embodiment.

In both embodiments, whether the protein compound is in preformed solution or as a dry powder, it is preferable to start from sterile preparations for the surgical applications.

This sterility can be obtained as long as the raw material is sterilized by filtration, by then working in a sterile environment (special sterile areas, presterilized equipment and in an isolated atmosphere).

It is, however, advantageous to be able to simplify the operating conditions and to decrease the complexity and cost thereof by adopting a validated process of final sterilization. Such a sterilization can be obtained by gamma or beta irradiation, preferably when the protein solution or powder has been supplemented beforehand with a "radioprotective" agent which traps free radicals, such as a sugar or a polysaccharide, in particular starch at a concentration close to 1%.

The polymerization/crosslinking time can be controlled according to the constituents used for the production of the adhesive matrix, in a way which is known per se.

In one embodiment of the invention, the adhesive matrix is produced using the mixture of a protein compound in solution, preferably of the native collagen, of the heated collagen or of the albumin, with an oxidized polysaccharide or mucopolysaccharide, preferably oxidized starch, oxidized dextran or oxidized hyaluronic acid.

The adhesive matrix can thus be prepared, according to a first embodiment of the invention, using a mixture of polyaldehyde and of heated collagen, in a ratio by weight of 1:10 to 1:160, preferably of 1:15 to 1:50, with a final concentration of heated collagen of 4 to 16%, preferably of 4 to 13% by weight. The temperature of the polysaccharide solution is preferably between +1° C. and +30° C., and that of the heated collagen solution at a value allowing its fluidification, namely between +37° C. and +50° C.

The temperature of the adhesive mixture is preferably between +35° C. and +41° C. The reaction time of the mixture can be adjusted as a function of the pH of the heated collagen, ranging between 6.5 and 7.5. A short polymerization time, less than 1 minute, can be obtained at pH 7.5 and can be gradually increased by acidifying the heated collagen solution to pH 6.5.

According to another embodiment of the invention, the adhesive matrix is prepared using a mixture of oxidized polyaldehyde and native collagen in a ratio by weight of 1:10 to 1:50, preferably of 1:10 to 1:30, with a final collagen concentration of 1 to 5%, preferably of 2 to 4%. The temperature of the oxidized polysaccharide solution is preferably between +1° C. and +30° C., and that of the native collagen solution between +18° C. and +37° C. The temperature of the adhesive mixture is preferably between +18° C. and +37° C. The reaction time of the mixture can be adjusted as a function of the pH of the collagen, between 6.5 and 7.5, and of the temperature of the mixture. The polymerization time increases when decreasing the pH and/or the temperature of the mixture.

According to another embodiment of the invention, the adhesive matrix is prepared using a mixture of powdered activated hydrophilic polymer and of heated collagen in solution, in a ratio by weight of 1:50 to 1:1, preferably between 1:10 and 1:1, with a final concentration of heated collagen of 4 to 20%, preferably between 10 and 18%. The temperature of the heated collagen solution is between +37° C. and +50° C., and the pH of the heated collagen solution can range from 6.9 to 9.0, according to the crosslinking time desired, from less than one minute to several tens of minutes. The temperature of the resulting adhesive mixture is preferably between +35° C. and +41° C.

According to yet another embodiment, a 1:4 mixture of oxidized polyaldehyde and albumin can be used.

According to one embodiment of the invention, the adhesive matrix can be prepared using proteins which have undergone oxidative cleavage.

In this case, treatment with periodic acid or a salt thereof, preferably sodium periodate, can be carried out according to a process known per se.

The collagen is particularly preferably for the purposes of the invention, and can be of any type mentioned previously. The preferences mentioned above also apply in this case.

The modification by oxidative cleavage of the collagen is described in U.S. Pat. No. 4,931,546.

This treatment causes cleavages in certain constituents of the collagen, hydroxylysine and sugars, and thus creates reactive sites (aldehyde groups) without causing the crosslinking thereof as long as the pH of the collagen solution remains acid.

The oxidized collagen can be conserved in lyophilized form, at a temperature of +4° C. to +25° C.

According to this embodiment, the polymerization/crosslinking agent then consists of a buffer at slightly alkaline pH to allow the crosslinking of the mixture, at neutral pH.

According to the invention, the adhesive matrix can thus be produced by mixing oxidized collagen in dehydrated form with a buffer in solution, the solution possibly, itself, resulting from the prior dissolving of a buffer in dehydrated form, in water.

According to another embodiment of the invention, proteins modified by an acylating or sulfonating agent can be used for the preparation of the adhesive matrix.

The proteins mentioned above and the preferences thereof also apply to this embodiment.

The polymerization/crosslinking agent is also, in this case, a buffer of slightly alkaline to neutral pH, preferably of between 6.0 and 9.0, more preferably of between 8.0 and 8.5.

The adhesive matrix is produced by a process similar to that mentioned above, by mixing the proteins with an acylating or sulfonating group with the buffer solution so that the acylation or sulfonation reaction can take place, producing the adhesive matrix.

According to another embodiment of the invention in which the adhesive matrix is based on fibrin glue, the glues currently available on the market, in particular those sold under the names "Tissucol®" or "Tisseel®", sold by Baxter, or "Beriplast®", sold by Centéon, can be used for the purposes of the invention.

It is a concentrated fibrinogen solution (70–140 mg/ml) containing factor XIII and, optionally, fibronectin.

In this case, the polymerization/crosslinking agent consists of a thrombin solution (4–100 I.U) to which collagen can optionally be added.

In accordance with the invention, whatever the type of adhesive matrix selected, the adhesive foam is prepared during the formation of the adhesive matrix.

When this results from the mixing of two basic constituents (protein compound—polymerization/crosslinking agent), in particular in the abovementioned cases, this mixture is prepared extemporaneously and before its application to tissues. During this operation, a gas is introduced by any process known to those skilled in the art.

The gas can be introduced in particular during the mixing of the constituents, or directly into the preformed mixture (i.e. into the fluid adhesive protein matrix material).

According to another embodiment of the invention, it is possible to envisage, in a less preferred way, carrying out the mixing of the two basic constituents in situ, i.e. the application of a preformed protein compound foam and then the subsequent application, in particular by spray, of the required polymerization/crosslinking agent.

The gas used for the purposes of the invention can consist of air or of one or more of the components thereof, for example nitrogen, oxygen, carbon dioxide.

The preferred gases are air, carbon dioxide and nitrogen.

It can be a gas or a mixture of gases (referred to hereinafter using the general term "gas").

In accordance with the invention, the gas used for the formation of the adhesive foam can be associated, preferably, with one of the basic constituents for the formation of the adhesive matrix, where appropriate with the protein compound which can be polymerized/crosslinked and/or with the polymerization/crosslinking agent, and/or supplied independently of one of these constituents.

The term "associated" refers to the case in which the gas is simply contained in the same recipient as the constituent of the adhesive matrix (powder/gas or liquid/gas phases), such as the case in which the gas is mixed with the polymerization/crosslinking agent, which is, for example, in pulverulent or lyophilized form.

When the gas is associated with one of the components for the adhesive matrix, the foam is formed during the mixing of said components for the production of the adhesive matrix.

The gas can also be supplied independently, alone or combined with a vehicle which is nontoxic, biocompatible and biodegradable and which is mixed with the adhesive matrix and the constituent elements thereof at the time of preparation of the adhesive foam.

It can be a protein compound such as that used for the formation of the adhesive matrix. However, in this case, the amount of protein compound being used as a vehicle is such that it cannot, on its own, allow the formation of the adhesive matrix.

The vehicle can reinforce or add to the activity of the foam, or have biological activity. It can in particular constitute, in parallel, a vehicle for one or more biologically substance(s) as indicated hereinafter.

In this case, the mixture for the formation of the adhesive matrix can be prepared beforehand (so as to produce the adhesive matrix material), and then the gas optionally combined with a vehicle as described above is then introduced into the adhesive matrix already in the process of forming.

The polymerization/crosslinking agent and/or the vehicle containing the gas is/are preferably in dehydrated form, in particular lyophilized form.

In a variant, the vehicle can be, in a less preferred way, in liquid form.

According to another aspect of the invention, other components which do not interfere with the formation of the foam can be incorporated.

The adhesive foam can thus allow the delivery of biologically active substances to the target site to which it is applied.

A large variety of biologically active substances can thus be mixed with the vehicle. Examples of such substances include, but in a nonlimiting way: drugs, vitamins, growth factors, hormones, steroid derivatives, antibiotics, vaccines, antiviral agents, antifungal agents, antiparasitic agents, antitumor agents, anticancer agents, toxins, enzymes, enzyme inhibitors, proteins, peptides, inorganic compounds (ex. zinc, copper, selenium, calcium derivatives), neurotransmitters, lipoproteins, glycoproteins, immunomodulators, immunoglobulins and fragments thereof, contrast agents, fatty acid derivatives, polysaccharides, nucleic acids (ex. DNA, RNA fragments) and polynucleotides.

Among the growth factors, the following factors or their corresponding genes are particularly preferred: factors of the type EGF (Endothelial Growth Factor), FGF (Fibroblast Growth Factor) and TGF-E (Transforming Growth Factor-E), including BMPs (Bone Morphogenetic Proteins), IGFs (Insulin-like Growth Factor), PDGFs (Platelet Derived Growth Factors) and VEGFs (Vascular Endothelial Growth Factors), or analogs and derivatives of these factors.

These biologically active substances can be mixed in solution with the vehicle, and then optionally dehydrated by any means known to those skilled in the art.

It is also possible to take a dehydrated vehicle up in a minimum volume of solution containing the biologically active substance(s) or to add a concentrated solution of this (these) biologically active substance(s) to a dehydrated vehicle.

Finally, less preferably, it is also possible to prepare an aqueous solution of the vehicle mixed with one or more biologically active substance(s) before being mixed with the gas.

Any process known to those skilled in the art can be used to prepare the foam, consisting simply in mixing various products and a gas in a homogeneous manner. The mixture is prepared extemporaneously before use so as to produce a ready-to-use adhesive foam.

For this purpose, the kits which form the subject of the present invention can be used.

The constituents required for the formation of the foam are preferably contained separately in syringes, the foam being produced by transferring the content back and forward from one syringe to the other until a homogeneous mixture is produced.

The foam harvested in a single syringe can then be applied to the desired site.

For this purpose, a kit such as that described in application WO 98/15299 for the preparation of a glue based on collagen and on macromolecular polyaldehyde can be used.

It is recalled that this kit can be in the form of two syringes containing the collagen component and the polyaldehyde, respectively.

These syringes are attached to a maintaining device equipped with mixing means designed to be able to extemporaneously mix their content in a homogenous manner, after having reheated the collagen syringe to the suitable temperature, of between 37° C. and 50° C. according to the desired fluidity.

The protein compound and the polymerization/crosslinking agent are packaged in one of the forms described above.

The required amount of gas is also present in one of the syringes or shared between each of them, such that the gas is introduced at the time of formation of the adhesive matrix material by mixing of the constituents.

In a variant, the required amount of gas, optionally combined with a vehicle as described above, can originate from another syringe, in which case it is introduced into the adhesive matrix material in the process of forming for example by polymerization/crosslinking, after mixing of the basic constituents, this premixture forming the adhesive matrix material possibly, itself, being produced using the kit according to application WO 98/15299.

When it is mixed with a vehicle, optionally combined with one or more biologically active substance(s), the gas represents preferably a minimum of 50% of the total volume of the preparation, and more preferably 90% of the total volume.

The mixing takes place preferably while incorporating a volume of gas representing 25 to 90% of the total volume of the foam, preferably from 40 to 75%.

This mixing takes place, moreover, at a temperature which promotes the incorporation of the gas into the biological glue. This temperature is preferably physiological, more preferably between 18° C. and 41° C.

Where appropriate, this mixing takes place at the very start of the crosslinking, preferably when the initial viscosity of the mixture is lowest.

The foams produced in accordance with the invention have adhesive properties which are satisfactory for use in surgery and/or in therapeutics, and which are comparable to those of the known biological glues based upon which they are prepared.

They must be used straight away, within the first five minutes of the preparation.

According to the constituent elements of the adhesive matrix and the method of production thereof, it is possible, in a known way, to control the polymerization/crosslinking time so as to allow the formation of the foam and its application to the desired site.

The adhesive foam which is the subject of the present invention is applied immediately after its formation, when it is still in the process of polymerizing/crosslinking.

It can be applied by processes known to those skilled in the art. It can preferably be injected, through syringes, catheters, cannulas or any other equivalent material which allows the foam to flow easily. In particular, for cylindrical devices, the interior diameter can be between 0.1 and 2 mm. The injection system can comprise an applicator, the form of which is particularly suitable for the desired use.

According to another embodiment of the invention, the foam can be formed in situ by subsequent application of the required constituents as mentioned above.

The foam can lose its sticky nature after polymerization/crosslinking, allowing selective and accurate application to the target tissues without gluing the undesired tissues neighboring the site of intervention.

The rate of setting of the adhesive matrix in the foam structure is not affected by the introduction of gas.

The adhesive foam according to the invention is nontoxic and is perfectly well tolerated by the host organism, while at the same time being more elastic than the known glues.

The final foam density is variable according to the amount of gas introduced and the application envisaged.

It is characterized by the presence of pores with a diameter of generally 50 and 200 microns.

This porosity confers on the product remarkable properties with respect to blood platelets, which can adhere thereto more rapidly due to the large exterior surface area of contact. An aggregate of activated platelets which secrete the clotting factors required for hemostasis forms. The adhesive matrix thus acquires, due to this porosity, hemostatic properties which enable bleeding to be stopped through the combined action of the mechanical sealing of the wound and of the platelet activation on contact with the blood.

This porosity confers great elasticity on the adhesive matrix, which makes it a product of choice for sealing lung wounds and stopping air leaks, while at the same time producing local hemostasis after exeresis of a tumor.

The porosity of the adhesive material facilitates its cellular colonization, its biodegradation and its transformation into cicatricial tissue, while at the same time avoiding the formation of postoperative adhesions with the organs adjacent to the wound.

The deposits of foam on the live tissues are in particular easier to visualize due to their particular microporous structures and their opacity.

Due to its low density, it can be applied with great accuracy to the tissues, without experiencing the problems of running conventionally encountered with the liquid biological glues, or the risks of dispersion of the glues by the propellant gases of the sprays.

Its initial fluidity allows its injection with the aid of syringes and its use by laparoscopy with the aid of suitable cannulas and catheters. It can be easily spread using a spatula or a brush by painting in open surgery such as in laparoscopy.

This porous tissue adhesive is therefore particularly indicated for producing hemostasis of vascular or tissue, surgical or traumatic wounds, protecting them and facilitating the cicatrization thereof, while avoiding the formation of postoperative adhesions.

The adhesive foam according to the invention can be used, in a nonlimiting way, for preventing or stopping the bleeding of vascular or tissue wounds, for attaching biological tissues, including live tissues, to each other or to an implanted biomaterial, for cicatrizing surgical or chronic wounds, protecting or sealing sutures, preventing the formation of postoperative adhesions, delivering biologically active substances in particular with medicines for local application and filling tissue cavities (bone, cartilage, skin lesions, etc).

A subject of the invention is also, therefore, the surgical or medical treatment processes comprising the emplacement, in a suitable site of the organism, via a suitable route of access, of an amount of foam according to the invention which is effective for adhering to the site and causing the desired effect.

The invention thus provides a process for protecting or attaching biological tissues, including live tissues, to each other or to an implanted biomaterial having functions which are reactive with respect to one of the constituents of the adhesive matrix, comprising mixing the constituents (constituents of the adhesive matrix and gas) required for the formation of the: foam, simultaneously or successively as mentioned above.

The resulting fluid foam is then applied rapidly, i.e. in less than 3 minutes, during the polymerization/crosslinking of the adhesive matrix, to said tissues and/or said biomaterial at a temperature of between 20° C. and 41° C., and then all of this is left to polymerize/crosslink.

The mixing prior to the application can be carried out with the kit described above.

The polymerization/crosslinking time can be adjusted as a function of the constituents of the adhesive matrix and of their conservation, in a way known per se, varying the pH, the concentrations and the temperature.

The in vivo resorption time can also be adjusted, in particular by chemically modifying the basic constituents of the adhesive matrix, as is known in the art, or by controlling the concentration of polymerization/crosslinking agent.

According to the composition of the adhesive matrix, this time can vary from a few days to several months.

According to the applications, the implanted biomaterial consists of the adhesive foam itself, which is then used alone.

In other cases, it can involve attaching a biomaterial having, for example, amine-containing functions which are reactive with respect to the constituent polyaldehyde of the adhesive matrix.

For other applications, in particular the prevention of postoperative adhesions, the adhesive foam according to the invention can be used alone or be tightly attached to a film based on collagen, so as to form a bicomposite material.

It can be a collagen film as described in

The collagen used to form the film corresponds to that mentioned above for producing the foam. The heated collagen is preferred.

The collagen film can also comprise a hydrophilic additive, preferably chemically unreactive with respect to the collagen, i.e. which is not capable of reacting with the collagen present, in particular which forms no covalent attachments with it during the crosslinking.

The hydrophilic additive preferably consists of polyethylene glycol.

The preparation of the biocomposite material itself is carried out by assembling the film-forming layer and the adhesive foam in the process of forming or once formed, i.e. after mixing of the required constituents.

The assembly comprises pouring the collagent solution, intended to produce the film, onto a suitable substantially flat support, distributing it evenly.

The support is inert in that it does not react with the abovementioned components and is not involved in the crosslinking process. It is preferably hydrophobic, for example made of PVC or polystyrene.

However, this support can also consist of a strippable material which will remain slightly adherent and which may then be separated at the time of surgical use.

This support can itself also consist of a film, for example of dried collagen, onto which the solution is poured, or a layer of collagen material gel in a distinctly more advanced state of gelling.

The density of the thin layer applied is preferably between 0.1 and 0.3 g/cm$^2$.

This collagen solution is poured at a temperature advantageously of between 4 and 30° C., preferably between 18 and 25° C.

This solution is left to gel and the foam prepared as mentioned above is applied to said solution in the process of gelling. In other words, the layer of porous foam is deposited onto the gel, with application continuing by simple gravity or, optionally, by slight compression which is insufficient to cause any appreciable compaction of the foam.

The moment at which the porous foam is applied to the solution in the process of gelling is such that the gel is still soft and allows the porous foam to penetrate over a distance which is advantageously of the order of 0.05 to 2 mm, preferably of the order of 0.1 to 0.5 mm.

In general, when the solution which is gelling is at a temperature of between 4° C. and 30° C., the porous foam layer is applied between 5 and 30 minutes after the solution has been distributed over the surface holding it.

This is left to dry or is lyophilized in order to obtain the biocomposite material according to the invention.

The polymerization/crosslinking of the adhesive matrix can take place or come to an end, where appropriate, during the drying of the bicomposite material.

This drying can be obtained at a temperature of between 4° C. and 30° C., preferably between 18° C. and 25° C.

The drying of the material can be carried out in a stream of sterile air, if necessary.

After drying, the bicomposite material according to the invention can be separated from its support. In a variant, it can comprise or incorporate a film or a layer of collagen material onto which the collagen solution has been poured.

The bicomposite material according to the invention is stable at room temperature and remains stable for long enough to be handled at temperatures possibly rising to 37–40° C.

The thickness of the collagen film is preferably less than 100 µm, and more preferably between 30 and 75 µm.

The thickness of the foam is preferably between 0.2 cm and 1.5 cm, even more preferably between 0.3 cm and 1.2 cm.

Such a bilayer material exhibits a set of particularly surprising hemostatic, anti-postoperative adhesion and biodegradability qualities.

The bicomposite collagen material according to the invention is particularly suitable for preventing postoperative adhesions, in particular to hemorrhagic wounds, because the film prevents adhesions, the composite material adheres well to such wounds and there is no blood at the interface.

Besides its properties of hemostasis and of prevention of postoperative adhesions, the collagen material from the present invention facilitates cicatrization because of its composite structure, combining a highly porous layer of foam with a collagen film.

The porous part of the material can easily be colonized by the surrounding cells. The film protects the ongoing cicatrization for a few days due to its properties of forming a barrier to bacteria and microorganisms.

The power of the film of the material to prevent adhesions is also reinforced by the layer of foam of the material accelerating the cicatrization of the wound.

According to the invention, the bicomposite collagen material is thus useful for hemostasis and preventing postoperative adhesions to bleeding wounds, while at the same time facilitating healing.

In addition, the macromolecular hydrophilic additive is eliminated by diffusion through the collagen material, in a few days, the swelling of this material promoting the degradation of the collagen film in less than a month.

The bicomposite material according to the invention can also be used to promote cicatrization. Its very open porous structure allows rapid cellular colonization. With regard to the film, it makes it possible to isolate the porous part in order to make it accessible to specific cells.

By way of example, fibroblasts can be cultured in the porous part of the material, in vitro, and epithelial cells can be cultured on the film, by creating two temporarily separate compartments.

The invention will be described in more detail with the aid of the examples given hereinafter by way of nonlimiting indication.

EXAMPLE 1

Adhesive Foam Consisting of an Adhesive Matrix Combining Heated Collagen and Oxidized Starch (GOS Glue)

Preparation of the Oxidized Starch:

A solution of soluble starch is prepared, at the concentration of 20% and at the temperature of 75° C., until a totally homogenous solution is obtained, and then is diluted two-fold. It is then prefiltered and filtered through a membrane with a porosity of 0.22 µm.

The pH of the starch is then adjusted to pH 3.0–3.2 and the concentration of the starch is 6%. Next, sodium metaperiodate at the final concentration of 0.36 M is added to the solution of oxidized starch at room temperature. After 2 hours of treatment, the solution is dialyzed, with a membrane which has a cut-off threshold ranging from 5 to 10 kDa, against ultrafiltered demineralized water. The dialysis is continued until total elimination of the dialyzable products of the oxidation reaction and of the reagents, as well as of the iodinated derivatives, formed during the reaction.

Next, the concentration of the solution of oxidized starch is adjusted to the desired value, between 1 and 3%. It is prefiltered and filtered sterily through a membrane which has a porosity of 0.22 µm.

The product is stable for at least a year, at a temperature of +4° C. to +25° C., in the absence of air.

For the preparation of an adhesive foam, the solution of oxidized starch can be packaged in syringes.

The solution of oxidized starch, packaged in syringes or in bottles, can also be lyophilized under sterile conditions and conserved at a temperature of +4° C. to +25° C., in the absence of air.

Subsequent dissolving of the lyophilized oxidized starch makes it possible to prepare, if necessary, more concentrated solutions of oxidized starch which can reach 3 to 30%.

Preparation of the Heated Collagen:

The collagen used is from a source known to those skilled in the art. If it is bovine type I collagen, it can be acid-soluble or solubilized by digestion with pepsin. If it is collagen from human placenta, it can be prepared by extraction with pepsin, according to the process described in patent EP-A-0 214 035.

A mixture of types I and III is, for example, obtained. This can then be optionally used to separate the type I and/or the type III. The collagen can also be prepared by genetic recombination techniques.

An acid solution of collagen at a concentration of 4 to 16% is prepared by gradually adding an acid collagen powder to water, at a temperature of 42° C. Very rapidly, after 2 to 5 minutes of stirring, as soon as the fluidity allows, the solution is neutralized with a molar solution of sodium hydroxide, at a pH ranging from 6.5 to 7.5.

After neutralization, the temperature of the collagen solution is adjusted to +60° C. so as to allow it to be sterilized by filtration through a membrane which has a porosity of 0.22 µm, subsequent to prefiltration.

For use in a kit, in particular as described in application WO 98/15299, the collagen is then distributed sterily into syringes and is conserved at a temperature of between +4° C. and +25° C., and is stable for at least a year.

In one variant, the solution of heated collagen is supplemented with starch at 1% or other agents which filtered at a temperature of 42° C. through a membrane which has a porosity of 0.22 microns and distributed into syringes which can be sterilized by gamma irradiation, ultimately at a dose of 5 to 30 kilogreys.

Preparation of the GOS Adhesive Foam

A 5 ml heating syringe, filled with 2 ml of heated collagen at a concentration of 16% and wrapped with a resistant film equipped with a thermostat which allows the temperature of the collagen to be maintained between +44° C. and +50° C., is prepared. A 5 ml syringe containing 2.5 ml of air and 0.5 ml of oxidized starch is also prepared.

Next, the content of these two syringes linked by a simple connector is mixed by alternately totally emptying the content of one into the other, 10 to 20 times until a completely homogeneous adhesive foam is produced.

According to another variant of preparation of the adhesive foam, a 2.5 ml heating syringe, filled with 2 ml of heated collagen at a concentration of 16% and wrapped with a resistant film equipped with a thermostat which allows the temperature of the collagen to be maintained between +44° C. and +50° C., is prepared. In addition, a syringe containing 0.5 ml of oxidized starch is prepared. These two syringes are assembled in a kit as described in patent application WO 98/15299. They are brought together via a connector/mixer setup, the function of which is to produce a perfectly homogeneous adhesive gel. The content of the kit is transferred into an empty 5 ml syringe with the aid of a simple connector. In parallel, a 5 ml syringe containing 2.5 ml of air is prepared.

Next, the content of these two syringes is mixed as described above.

According to another variant, it is possible to the previous one. For this, a kit for biological 'glue' is assembled using a 2.5 ml syringe filled with 2 ml of heated collagen at a concentration of 16% and a syringe containing 0.5 ml of oxidized starch. The content of this kit is discharged into a 10 ml syringe. In addition, a 10 ml syringe containing 7.5 ml of air is Next, the content of the two syringes is mixed according to the process described above.

EXAMPLE 2

Foam Consisting of an Adhesive Matrix Prepared Using "GOS Glue" and Native Collagen Preparation of the Native Collagen A solution of collagen at 3% in ultrafiltered demineralized water is prepared. Next, a solution of 0.22 M disodium phosphate is added so as to obtain a final concentration of 20 mM. The collagen suspension is homogenized with a deflocculating blade mixer, and then its pH is adjusted to 7.4–7.5 with a concentrated solution of hydrochloric acid.

The neutralized collagen suspension is then diluted with demineralized ultrafiltered water so as to attain a collagen concentration of 1.8% and a phosphate concentration of 13 mM. It is left to stand overnight so as to obtain complete fibrillation of the collagen.

The following day, the collagen suspension is centrifuged at 10,000–15,000 G in order to concentrate the collagen precipitate, which is then homogenized with a defloculating blade mixer. Two grams of 2% by weight collagen precipitate are distributed into 5 ml syringes which are lyophilized under conditions known to those skilled in the art.

After the lyophilization, the plunger is introduced into the syringes of collagen, without compressing the collagen. These syringes, which are sterilized by gamma irradiation at a dose of 25 to 35 Kgy, are packaged in an airtight double wrapping.

Two other main variants can be used for a) The suspension of 2% collagen precipitate is supplemented with 1% of starch before lyophilization, which makes it possible to decrease the hydrolytic effects of the sterilizing final irradiation on the collagen molecule.

b) The collagen suspension is prepared sterily throughout the process in order to avoid the sterilizing final irradiation.

Other variants of this process are to introduce greater or lower amounts and concentrations of collagen.

Preparation of the Elements of the "GOS Glue"

The elements of the GOS glue are prepared as described in Example 1 and comprise a syringe of heated collagen at a concentration of 8% and a syringe of oxidized starch at a concentration of 1.5%.

Preparation of the GOS/Native Collagen Adhesive Foam

As described in the previous example, the mixture of the heated collagen and of the oxidized starch (GOS glue), at the respective concentrations of 8 and 1.5%, is first prepared. For this, it is possible to use a kit as described in application WO 98/15299 and to transfer 2.5 ml of gel into a 5 ml syringe. It is also possible to use two 5 ml syringes linked by a simple connector, one containing 2 ml of heated collagen at 8% and the other containing 0.5 ml of oxidized starch at 1.5%. The mixing of the two products is carried out by alternately totally emptying the content of one of the two syringes into the other, 5 to 10 times until a completely homogeneous gel is The collagen used for this example is bovine type I collagen extracted from calf dermis, optionally solubilized by digestion with pepsin and purified by saline precipitations, according to the techniques already described. Similarly, it is possible to use type I or type III collagens of other animal species or of human origin, or collagen of recombinant origin or other types of collagen, or a mixture thereof in any The syringe of lyophilized collagen is then connected to the syringe of mixed GOS glue. The two glue into the syringe containing the lyophilized collagen, and then transferring the content from one syringe to the other by pushing their plungers back and forward 10 to 20 times until a homogeneous foam is Once the GOS glue is prepared, the foam must be entirely polymerized, in order for it to be able to adhere to the tissues.

EXAMPLE 3

Foam Consisting of an Adhesive Matrix Prepared Using GOS Glue and Native Collagen Mixed With FGF (Fibroblast Growth Factor)

The GOS glue is prepared as described in the and 0.5 ml of oxidized starch at 1.5%. It is transferred into a 5 ml syringe.

100 to 250 $\mu$l of a solution of recombinant human FGF are added to the syringe of native collagen.

Then, this syringe of native collagen is mixed with the GOS glue, as described previously, until a homogeneous GOS/native collagen-FGF foam is produced.

According to another variant, the FGF is allowed to adsorb to the native collagen for a period of time, from 5 to 120 minutes, before mixing the collagen/FGF preparation with the GOS glue.

Another variant of this example consists in lyophilizing the FGF with the native collagen according to the process below. The collagen precipitate is mixed with a solution of FGF and this is homogenized, distributed into 5 ml syringes, in a proportion of 2 g sterilized by gamma irradiation. This syringe of lyophilized collagen and FGF is mixed with 2.5 ml of GOS glue, as described in example 2, until a homogeneous foam is produced.

The composition of this adhesive foam is particularly used for filling nerve lesions, FGF being a factor which facilitates nerve regeneration.

In this example, the FGF can be replaced with other growth factors, or mixtures thereof, which have activities equivalent to FGF.

EXAMPLE 4

Foam Consisting of an Adhesive Matrix Prepared Using GOS Glue and Native Collagen Mixed With IL-2 (Type II Interleukin)

Example 3 is repeated, replacing the FGF or equivalent factors with IL-2.

This GOS/native collagen-IL-2 adhesive foam is cancerogenesis and the inhibition of the development of tumors. It can also be prepared with other products, alone or mixed, which inhibit the development of cancers and of tumors.

EXAMPLE 5

Foam Consisting of an Adhesive Matrix Prepared Using GOS Glue and Native Collagen Mixed With Cellular Growth or Tissue Regeneration Factors Examples 3 and 4 can be repeated with native collagen mixed with any cellular growth or tissue regeneration factor, so as to prepare adhesive foams which are active on skin, bone, cartilagenous, etc wounds.

EXAMPLE 6

Adhesive Foam Prepared Using Collagen in Dry Powder Form

Preparation of the Collagen

An acid solution of collagen is prepared at a concentration of 2% by gradually adding an acid collagen powder to water, at a temperature of 20–25° C. As soon as the solution is completely homogeneous, the collagen is neutralized by adding sodium phosphate, at the final concentration of 10 mM, to attain a pH of 6.5–8. The solution of collagen is then left to stand overnight at 20–25° C., and then the precipitated collagen is recovered by centrifugation. It is desalified and dehydrated with a series of acetone washes: in the order, 1 bath of 90/10, m/m, acetone/water; 3 baths of 80/20, m/m, acetone/water and 3 baths of 100% acetone.

The collagen is then distributed, in a volume of 2.5 ml, into 5 ml syringes, in a proportion of 80–400 mg of dry collagen per syringe. The collagen used is from a source known to those skilled in the art including recombinant collagens. If it is bovine type I collagen, it can be acid-soluble or solubilized by digestion with pepsin. If it is collagen from human according to the process described in patent EP-A-0 214 035.

The collagen, after an initial sterilizing filtration, can be prepared sterily throughout the known to those skilled in the art.

In one variant, the collagen distributed in a Becton-Dickinson syringe ref: "STERIFILL" can be sterilized by gamma irradiation at the dose of 5 to 35 kilogreys, preferably in the presence of an agent which protects against the hydrolytic effects of irradiation, such as starch. An additional volume of air is incorporated into the syringe, if necessary, in order to increase the future volume of the foam.

Preparation of a syringe of sterile distilled water or physiological buffer, according to conventional methods, using the same Becton-Dickinson syringe. This syringe can also contain a supplementary volume of air. Advantageously, one of the two syringes is equipped or associated with a heating system which allows the temperature to be regulated from 30° C. to 50° C.

Preparation of the Foam

After heating one of the two syringes, it is connected to the other syringe with the aid of a connector with an interior diameter close to 2 mm, large enough to avoid plugging by initial lumps and The content of the liquid syringe is sent into the syringe containing the powder, and the mixing is carried out by successive transfers, 10 to 20 times, at a temperature lower than 37° C. when the aim is to conserve the helical structure of the collagen, and from 37° C. to 50° C. when the aim is to produce a decrease in or an elimination of the helical structure.

When the foam is homogenized, it is conserved in one of the two syringes (at warm or room temperature depending on the syringe used), before being mixed with a sterile syringe containing the oxidized starch, at room temperature, prepared as in the previous example.

After incorporation of the oxidized starch into the above foam, the final foam is used at a temperature lower than 40° C., most commonly close to 37° C., and must be used within the next five minutes while it is still sufficiently fluid.

The rate of crosslinking can easily be controlled by adjusting the pH of the collagen used and its concentration.

In variants, one or more biological product(s) antibiotics, anti-inflammatory agents, growth factors, etc, can be added to the syringe of collagen powder or to the syringe containing the aqueous solution for taking it up.

EXAMPLE 7

Adhesive Foam Consisting of an Adhesive Matrix Combining Albumin and Oxidized Starch (AOS Glue)

A solution of oxidized starch at 10 to 25% is

Preparation of the Albumin

The albumin used is from a known source. It is of human or animal origin or derived from genetic recombination techniques.

The albumin is taken up at a concentration of to 50%, neutralized at pH 6.5–7.5 with concentration solutions of sodium hydroxide and of hydrochloric acid, and filtered sterily through a membrane which has a packaged in 5 ml syringes.

The albumin syringe and a syringe containing 0.5 ml of oxidized starch at 10 to 25% are assembled in a kit, according to the process described in example 1. The kit is called AOS.

Preparation of the AOS/Native Collagen Adhesive Foam

As described in the previous examples, the mixture of the albumin and of the oxidized starch, at the respective concentrations of 20–50% and of 10 to 25%, can first be prepared, without introducing any air. For this, it is possible to use a kit similar to that used for preparing the GOS glue in example 2, and to transfer 2.5 ml of gel into a 5 ml syringe.

The syringe of AOS glue is then connected to a 5 ml syringe containing 2.5 ml of air. The two products are homogenized, beginning by passing the air into the syringe containing the AOS glue, and then transferring the content from one syringe to the other by pushing their plungers back and forward 10 to 20 times until a homogeneous foam with a volume of 5 ml is produced.

It is also possible to use two 5 ml syringes linked by a simple connector, one containing 2 ml of albumin at 20–50% and the other containing 0.5 ml of oxidized starch at 10 to 25% and 2.5 ml of air. The mixing of the two products is carried out by alternately totally emptying the content of one of the two syringes into the other 5 to 10 times until a completely homogeneous foam is produced.

Once the AOS glue is prepared, the foam must be entirely polymerized, in order for it to be able to adhere to the tissues.

EXAMPLE 8

Adhesive Foam Prepared Using Dehydrated Albumin and Oxidized Starch in Solution

Preparation of the albumin 0.4 to 1.25 g of powdered albumin are packaged sterily in a 5 ml Becton-Dickinson syringe, ref: "STERIFILL".

Preparation of a 2 ml syringe of distilled water or of physiological solution, PBS, associated with a heating system which makes it possible to bring the temperature of the liquid to between 37 and 45° C.

The two syringes are then connected end-to-end with the aid of a connector with a diameter of 1 to 2 mm.

The content of the two syringes is then mixed by successive transfers from one into the other. After 10 to 20 transfers, the homogeneous albumin foam is harvested in one of the two syringes.

This is then connected to a syringe containing 0.5 ml of oxidized starch at 6% and, after mixing by successive transfers from one of the syringe into the other, the adhesive protein foam can be applied to the wound to be treated.

EXAMPLE 9

Adhesive Foam Consisting of an Adhesive Matrix Combining the Albumin and Polyethylene Glycol Derivatives Bearing Activated Electrophilic Groups Which are Reactive With Respect to Amines The albumin is taken up at a concentration of to 50% and neutralized at pH 6.5–9 as described in example 7 or 8. 2 ml of this solution are then packaged in 5 ml syringes.

Among the activated electrophilic PEGs, use may equally be made, alone or mixed in any proportions, of SPA-PEG (succinimidyl propionate PEG), SCM-PEG (succinimidyl ester of carboxymethylated PEG) and BTC-PEG (benzotriazole carbonate of PEG), of molecular weight higher than 1000 Da, PEG derivatives, products sold by Shearwater Polymers. PEG-SS2 (disuccinimidyl succinate PEG), synthesized as described in patent application WO 96/03159 (Minnesota Mining and Manufacturing Company), can also be used. 40 to 500 mg of activated PEG in dehydrated form are packaged per 5 ml syringe.

Preparation of the Adhesive Foam

The mixing of the albumin and of the activated PEGs is carried out by transferring the entire content of the albumin syringe into the PEG syringe, and then totally emptying the content of one of the two syringes into the other 5 to 10 times until a totally homogeneous gel of 5 ml is produced.

Once the glue combining the albumin and the electrophilic derivatives of activated PEG is prepared, the foam must be prepared and used before the glue is entirely polymerized, in order for it to be able to adhere to the tissues.

The rate of polymerization, and therefore the time available for using the product, is regulated by the pH of the mixture. The more acid the pH, the slower the reaction and the longer the time available.

EXAMPLE 10

Adhesive Foam Consisting of an Adhesive Matrix Combining the Albumin and Activated PEG Derivatives Which are Reactive With Respect to Sulfhydryls The albumin is taken up at a concentration of 20 to 50% and neutralized at pH 6.5–9 as described in the previous examples. 2 ml of this solution are then packaged in 5 ml syringes.

Among the activated PEGs which are reactive with respect to sulfhydryls, use may equally be made, alone or mixed in any proportions, of VS-PEG (vinylsulfone PEG), MAL-PEG (maleimide PEG) and OPSS-PEG (orthopyridyl disulfide PEG), of molecular weight higher than 1000 Da, PEG derivatives, products sold by Shearwater Polymers. 40 to 500 mg of activated and dehydrated PEG are packaged per 2 ml syringe.

The adhesive foam is then prepared as described in example 9.

EXAMPLE 11

Adhesive Foam Consisting of an Adhesive Matrix Combining the Heated Collagen and Electrophilic Groups Which are Reactive With Respect to Amines Example 9 is repeated, replacing the albumin with the heated collagen prepared as described in example 1 at the concentration of 10–20%, at pH 6.5–9, and packaging two times less activated and dehydrated PEG per 5 ml syringe, i.e. 20–250 mg of PEG.

EXAMPLE 12

Adhesive Foam Consisting of an Adhesive Matrix Combining the Heated Collagen and Activated PEG Derivatives Which are Reactive With Respect to Sulfhydryls Example 10 is repeated, replacing the albumin with the heated collagen prepared as described in example 1 at the concentration of 10–20%, at pH 6.5–9, per 5 ml syringe, i.e. 20–250 mg of PEG.

EXAMPLE 13

Adhesive Foam Consisting of an Adhesive Matrix Prepared Using a Fibrin Glue and Agarose Gel Preparation of the Agarose Gel (Vehicle)

The agarose is taken up in solution in apyrogenic demineralized water, at the final concentration of 0.5–5% and at a temperature of between 75° C. and 100° C., and then the pH of this solution is adjusted to pH 7.5–9 with a concentrated phosphate buffer so as to produce a final concentration of transferred per 5 ml syringe. This solution is then lyophilized under conditions known to those skilled in the art.

In another variant, the solution of agarose is with 10–20 mM of borax at pH 7.5–9 or with a 1:1, mol/mol mixture of borax and of phosphate, at a final concentration of 10–20 mM.

After the lyophilization, the plunger is introduced into the syringes without compressing the agarose. These syringes, which are sterilized by gamma irradiation at a dose of 25 to 35 KGy, are packaged in an airtight double wrapping.

Another variant of this process is to filter the solution of agarose sterily, while hot—i.e. as soon as the viscosity of the solution is sufficiently low to allow it to be sterilized by filtration, after adjusting its pH to 7.5–9, as mentioned above, through membranes which have a porosity of 0.22 to 0.45 $\mu$m. This solution is then distributed sterily into 5 ml syringes, in a proportion of 2 ml per syringe, and lyophilized. After the lyophilization, the plunger is introduced into the syringes without compressing the agarose. The syringes are packaged in an airtight double wrapping. All the operations performed after the sterilizing filtration are carried out under sterile conditions known to those skilled in the art.

Preparation of the Fibrin Glue/Agarose Adhesive Foam

The fibrin glue is first prepared extemporaneously. All commercially available fibrin glues may be suitable. It may be, for example, a solution of TISSUCOL®containing fibrinogen. 2 ml of fibrin glue solution prepared extemporaneously are transferred into a 5,ml syringe and heated to 40° C.

The syringe of lyophilized agarose is then connected to the syringe of fibrin glue. The two fibrin glue into the syringe containing the lyophilized agarose, and then transferring the content from one syringe to the other by pushing their plungers back and forward 10 to 20 times until a homogeneous foam is Once the fibrin glue is prepared, the foam must be prepared and used before the fibrinogen is completely transformed into fibrin.

EXAMPLE 14

Adhesive Foam Consisting of an Adhesive Matrix Prepared Using Fibrin Glue, Agarose and an Antibiotic Example 11 is repeated, adding 0.25–2.5 mg of vancomycin, an antibiotic which is effective against Gram-positive bacteria, in particular Staphylococcus aureus and Staphylococcus epidermidis, the two main agents of graft infection in vascular surgery, to 2 ml of agarose solution before it is lyophilized.

This formulation is used to seal vascular anastomosis sutures.

One variant of this example is to include other antibiotics, alone or mixtures thereof in any proportions, in place of the vancomycin.

What is claimed is:

1. A kit for preparing a biocompatible fluid adhesive protein foam, which is bioresorbable and nontoxic, for surgical and/or therapeutic use, in particular for protecting/cicatrizing tissue wounds and attaching biological tissues to each other or an implanted biomaterial, said kit comprising:

a potentially adhesive protein compound which can be polymerized/crosslinked, solubilized in aqueous medium, in a first container;

a polymerization/crosslinking agent for forming a biocompatible fluid adhesive protein matrix, which is bioresorbable and nontoxic, in a second container;

a biocompatible and nontoxic gas or mixture of gases, either in the first, second and/or a third container;

optional means for extemporaneously mixing the constituents, protein compound in aqueous solution and polymerization/crosslinking agent for forming the adhesive matrix, and, said gas or mixture of gases;

whereby the protein foam is obtained in a ready to use form.

2. The kit of claim 1, wherein the first container contains the potentially adhesive protein compound in pulverulent, dehydrated and optionally in a sterilized form, the second container contains an optionally sterile buffered aqueous solution, and wherein the kit further comprises means for supplying a polymerization/crosslinking agent to the solubilized protein compound and means for mixing the content of the first and second containers, and means for using a gas in the mixture and producing the foam.

3. The kit of claim 1, wherein the polymerization/crosslinking agent is a reactive polymer and the gas is selected from air, nitrogen, oxygen and carbon dioxide or the mixture of one or more of these gases.

4. The kit of claim 1, wherein the kit is in the form of two syringes equipped with mixing means, in which one of the syringes contains the protein compound in aqueous solution and the other contains the polymerization/crosslinking agent.

5. The kit of claim 1, wherein the gas is combined with the protein compound and/or with the polymerization/crosslinking agent.

6. The kit of claim 2, wherein the mixing means make it possible to pass the mixture from one syringe to the other several times so as to ensure the formation of the foam using the gas included in the syringe containing the pulverulent protein compound.

7. The kit of claim 1, wherein the gas is combined with a biocompatible and nontoxic vehicle.

8. The kit of claim 1, further comprising a third syringe containing the gas optionally combined with a vehicle.

9. The kit of claim 8, wherein the vehicle also contains one or more biologically active substances.

10. The kit of claim 1, wherein the polymerization/crosslinking agent and/or the vehicle is in lyophilized form.

11. The kit of claim 7, wherein biocompatible and nontoxic vehicle is formed from a protein compound which comprises a protein or a mixture of proteins selected from collagen, gelatin, albumin, elastin and fibrinogen.

* * * * *